US011718646B2

(12) United States Patent
Kopin et al.

(10) Patent No.: US 11,718,646 B2
(45) Date of Patent: *Aug. 8, 2023

(54) BOVINE ADRENAL MEDULLA PEPTIDE 8-22 COMPOUNDS AND METHODS OF USE THEREOF FOR TREATING PAIN

(71) Applicants: Tufts Medical Center, Boston, MA (US); Trustees of Tufts College, Medford, MA (US)

(72) Inventors: Alan S. Kopin, Wellesley, MA (US); Krishna Kumar, Cambridge, MA (US); Jamie Raudensky Doyle, Newton, MA (US)

(73) Assignees: Tufts Medical Center, Boston, MA (US); Trustees of Tufts College, Medford, MA (US)

( * ) Notice: Subject to any disclaimer, the term of this patent is extended or adjusted under 35 U.S.C. 154(b) by 283 days.

This patent is subject to a terminal disclaimer.

(21) Appl. No.: 17/121,869

(22) Filed: Dec. 15, 2020

(65) Prior Publication Data

US 2021/0101934 A1 Apr. 8, 2021

Related U.S. Application Data

(63) Continuation of application No. 15/774,451, filed as application No. PCT/US2016/061101 on Nov. 9, 2016, now Pat. No. 10,899,796.

(60) Provisional application No. 62/253,094, filed on Nov. 9, 2015.

(51) Int. Cl.
| | | |
|---|---|---|
| *A61K 38/10* | (2006.01) | |
| *A61K 38/33* | (2006.01) | |
| *C07K 7/08* | (2006.01) | |
| *C07K 14/665* | (2006.01) | |
| *C07K 14/68* | (2006.01) | |
| *C07K 19/00* | (2006.01) | |
| *C07K 7/00* | (2006.01) | |
| *A61K 47/54* | (2017.01) | |
| *A61K 47/65* | (2017.01) | |
| *A61K 47/60* | (2017.01) | |
| *A61P 25/00* | (2006.01) | |
| *A61K 38/34* | (2006.01) | |
| *C07K 7/64* | (2006.01) | |

(52) U.S. Cl.
CPC .............. *C07K 7/08* (2013.01); *A61K 38/10* (2013.01); *A61K 38/33* (2013.01); *A61K 38/34* (2013.01); *A61K 47/542* (2017.08); *A61K 47/60* (2017.08); *A61K 47/65* (2017.08); *A61P 25/00* (2018.01); *C07K 7/00* (2013.01); *C07K 7/64* (2013.01); *C07K 14/68* (2013.01); *C07K 19/00* (2013.01)

(58) Field of Classification Search
None
See application file for complete search history.

(56) References Cited

U.S. PATENT DOCUMENTS

| | | |
|---|---|---|
| 4,033,940 A | 7/1977 | Hughes et al. |
| 4,216,141 A | 8/1980 | Rivier et al. |
| 4,271,068 A | 6/1981 | Kamber et al. |
| 4,868,154 A | 9/1989 | Gilbard et al. |
| 5,596,078 A | 1/1997 | Andersson et al. |
| 5,726,287 A | 3/1998 | Andersson et al. |
| 5,922,680 A | 7/1999 | Fjellestad-Paulsen et al. |
| 5,990,273 A | 11/1999 | Andersson et al. |
| 6,242,565 B1 | 6/2001 | Kishida et al. |
| 2005/0208047 A1 | 9/2005 | Anderson et al. |
| 2012/0230975 A1 | 9/2012 | Foster et al. |
| 2016/0052982 A1 | 2/2016 | Cohen et al. |

FOREIGN PATENT DOCUMENTS

| | | |
|---|---|---|
| WO | WO 2008/033395 A2 | 3/2008 |
| WO | WO 2011/017564 A2 | 2/2011 |
| WO | WO 2014/168721 A2 | 10/2014 |
| WO | WO 2015/162486 A1 | 10/2015 |

OTHER PUBLICATIONS

Bader et al., "Mas and Its Related G Protein-Coupled Receptors, Mrgprs", Pharmacological Reviews, vol. 66, p. 1080-1105, 2014.
Beinborn et al., "Ligand Function at Constitutively Active Receptor Mutants Is Affected by Two Distinct Yet Interacting Mechanisms", Molecular Pharmacology, vol. 65, p. 753-760, 2004.
Bond et al., "Single-nucleotide polymorphism in the human mu opioid receptor gene alters b-endorphin binding and activity: Possible implications for opiate addiction", Proc Natl Acad Sci USA, vol. 95, p. 9608-9613, 1998.
Cantel et al. "Synthesis and Conformational Analysis of a Cyclic Peptide Obtained via i to i+4 Intramolecular Side-Chain to Side-Chain Azide-Alkyne 1,3-Dipolar Cycloaddition", J. Org. Chem., vol. 73, No. 15, p. 5663-5674, 2008,.
Chen T. et al. "Intrathecal sensory neuron-specific receptor agonists bovine adrenal medulla 8-22 and (Tyr 6)-gamma2-msh-6-12 inhibit formalin-evoked nociception and neuronal Fos-like immunoreactivity in the spinal cord of the rat", Neuroscience, 2006, vol. 141, No. 2, pp. 965-975.
Chou and Elrod, "Prediction of Membrane Protein Types and Subcellular Locations", Proteins vol. 34, p. 137-153, 1999.
Dong et al., "A Diverse Family of GPCRs Expressed in Specific Subsets of Nociceptive Sensory Neurons", Cell, vol. 106, p. 619-632, 2001.

(Continued)

*Primary Examiner* — Christine J Saoud
*Assistant Examiner* — Jon M Lockard
(74) *Attorney, Agent, or Firm* — Cooley LLP; Matthew Pavao; J. Nancy Costigliola

(57) ABSTRACT

The present disclosure relates to, among other things, compounds and methods for treating neuropathic pain, ocular pain, ocular inflammation, and/or dry eye and methods of detecting mutations in specific G-protein coupled receptors, such as missense mutations, and determining the extent to which these mutations alter the pharmacological response of the G-protein coupled receptor.

11 Claims, 8 Drawing Sheets

Specification includes a Sequence Listing.

(56) References Cited

OTHER PUBLICATIONS

Doyle et al. "A platform-based approach for peptide drug discovery: generating probes to understand and treat itch," The FASEB Journal, vol. 28, No. 1, Supp. Abstract 1054.1, 2014.

Doyle et al. "A two-step strategy to enhance activity of low potency peptides," PLoS One, vol. 9:e110502, p. 1-9, 2014.

Doyle et al. "Development of a membrane-anchored chemerin receptor agonist as a novel modulator of allergic airway inflammation and neuropathic pain," J Biol Chem, vol. 289, p. 13385-13396, 2014.

Doyle et al., "Naturally occurring HCA1 missense mutations result in loss of function: potential impact on lipid deposition", Journal of Lipid Research, vol. 54, p. 823-830, 2013.

Drenth and Waxman, "Mutations in sodium-channel gene SCN9A cause a spectrum of human genetic pain disorders", Journal of Clinical Investigation, vol. 117, p. 3603-3609, 2007.

Fertleman et al., "SCN9A Mutations in Paroxysmal Clinical Study Extreme Pain Disorder: Allelic Variants Underlie Distinct Channel Defects and Phenotypes", Neuron, vol. 52, p. 767-774, 2006

Fortin et al., "Discovery of Dual-Action Membrane-Anchored Modulators of Incretin Receptors", PLoS One 6:e24693, 2011.

Fortin et al., Membrane-tethered ligands are effective probes for exploring class B1 G protein-coupled receptor function, Proc Natl Acad Sci USA, vol. 106, p. 8049-8054, 2009.

Fortin et al., "The μ-Opioid Receptor Variant N190K Is Unresponsive toPeptide Agonists yet Can be Rescued by Small-Molecule Drugs", Molecular Pharmacology, vol. 78, p. 837-845, 2010.

Guan et al., "Mas-related G-protein-coupled receptors inhibit pathological pain in mice", Proc Natl Acad Sci USA, vol. 107, p. 15933-15938, 2010.

Harwood et al., "Membrane Tethered Bursicon Constructs as Heterodimeric Modulators of the *Drosophila* G Protein-Coupled Receptor Rickets", Molecular Pharmacology, vol. 83, p. 814-821, 2013.

Harwood et al., "Targeted inactivation of the rickets receptor in muscle compromises *Drosophila* viability", Journal of Experimental Biology, vol. 217, p. 4091-4098, 2014.

Heller et al. "Novel Probes Establish Mas-Related G Protein-Coupled Receptor XI Variants as Receptors with Loss or Gain of Function," J Pharmacol Exp Ther, vol. 356, p. 1-35 (originally p. 276-283) 2015.

Hu et al., "Structural basis of G protein-coupled receptor-G protein interactions", Nature Chemical Biology, vol. 6, p. 541-548, 2010.

Kopin et al., "Identification of a series of CCK-2 receptor nonpeptide agonists: Sensitivity to stereochemistry and a receptor point mutation", Proc Natl Acad Sci USA, vol. 100, p. 5525-5530, 2003.

Lembo et al., "Proenkephalin A gene products activate a new family of sensory neuron-specific GPCRs", Nature Neuroscience, vol. 5, No. 201-209, 2002.

Liu et al., "Sensory Neuron-Specific GPCR Mrgprs Are Itch Receptors Mediating Chloroquine-Induced Pruritus", Cell, vol. 139, p. 1353-1365, 2009.

Lotsch and Geisslinger, "Are μ-opioid receptor polymorphisms important for clinical opioid therapy?" Trends in Molecular Medicine, vol. 11, p. 82-89, 2005.

Ngo et al. "Computational complexity, protein structure prediction, and the Levinthal paradox", Merz and Le Grand (Eds.) The Protein Folding Problem and Tertiary Structure Prediction, p. 491-495, 1994.

Rana et al., "Genetic Variations and Polymorphimsms of G Protein-Coupled Receptors: Functional and Therapeutic Implications", Annu Rev Pharmacol Toxicol 41:593-624, 2001.

Reimann et al., Proc Natl Acad Sci USA vol. 107, p. 5148-5153, 2010.

Samama et al., "A Mutation-induced Activated State of the $\beta_2$-Adrenergic Receptor", Journal of Biological Chemistry, vol. 268, p. 4625-4636, 1993.

Schnolzer et al., "In Situ Neutralization in Boc-chemistry Solid Phase Peptide Synthesis", International Journal of Peptide Research and Therapeutics, vol. 13, p. 31-44, 2007.

Scott et al. "Production of cyclic peptides and proteins in vivo", PNAS, vol. 96, No. 24, p. 13638-13643, 1999.

Sikand et al., "BAM8-22 Peptide Produces Itch and Nociceptive Sensations in Humans Independent of Histamine Release", Journal of Neuroscience, vol. 31, p. 7563-7567, 2011.

Solinski et al., "Pharmacology and Signaling of MAS-Related G Protein-Coupled Receptors", Pharmacological Reviews, vol. 66, p. 570-597, 2014.

Tatemoto et al., "Immunoglobulin E-independent activation of mast cell is mediated by Mrg receptors", Biochemical and Biophysical Research Communications, vol. 349, p. 1322-1328, 2006.

Thompson et al., "G Protein-Coupled Receptor Mutations and Human Genetic Disease", Methods in Molecular Biology, vol. 1175, p. 153-187, 2014.

Tsai et al., "Human opioid μ-receptor A118G polymorphism may protect against central pruritus by epidural morphine for postcesarean analgesia", Acta Anaesthesiol Scand, vol. 54, p. 1265-1269, 2010.

Wells J.A. "Additivity of mutational effects in proteins", Perspectives in Biochemistry, vol. 29, No. 37, p. 8509-8517, 1990.

Wray, "The evolutionary significance of cis-regulatory mutations", Nature Reviews Genetics, vol. 8, p. 206-216, 2007.

Zhang and Bulaj, "Converting Peptides into Drug Leads by Lipidation", Curr Medicinal Chemistry, vol. 19, p. 1602-1618, 2012.

SEQUENCE LISTING

<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Artificial Polypeptide

<400> SEQUENCE: 1

```
Val Gly Arg Pro Glu Trp Trp Met Asp Tyr Gln Lys Arg Tyr Gly
1               5                   10                  15

<210> SEQ ID NO 2
<211> LENGTH: 18
<212> TYPE: PRT
<213> ORGANISM: Artificial Sequence
<220> FEATURE:
<223> OTHER INFORMATION: Artificial polypeptide

<400> SEQUENCE: 2

Val Gly Arg Pro Glu Trp Trp Met Asp Tyr Gln Lys Arg Tyr Gly Gly
1               5                   10                  15

Gly Lys

<210> SEQ ID NO 3
<211> LENGTH: 12
<212> TYPE: PRT
<213> ORGANISM: Artificial Sequence
<220> FEATURE:
<223> OTHER INFORMATION: Artificial polypeptide

<400> SEQUENCE: 3

Tyr Val Met Gly His Phe Arg Trp Asp Arg Phe Gly
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Artificial polypeptide

<400> SEQUENCE: 4

Val Gly Arg Pro Glu Trp Trp Ala Asp Tyr Gln Lys Arg Tyr Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Artificial polypeptide

<400> SEQUENCE: 5

Val Gly Arg Pro Glu Trp Trp Ala Asp Trp Gln Lys Arg Tyr Gly
1               5                   10                  15
```

BOVINE ADRENAL MEDULLA PEPTIDE 8-22 COMPOUNDS AND METHODS OF USE THEREOF FOR TREATING PAIN

RELATED APPLICATIONS

This application is a continuation of U.S. non-provisional patent application Ser. No. 15/774,451, filed on May 8, 2018 (now allowed), which is a National Stage Application, filed under 35 U.S.C. 371, of International Application No. PCT/US2016/061101, filed on Nov. 9, 2016, which claims priority to, and benefit of, U.S. provisional patent application No. 62/253,094, filed on Nov. 9, 2015. The contents of each of these applications are hereby incorporated by reference in their entireties.

INCORPORATION-BY-REFERENCE OF SEQUENCE LISTING

The contents of the text file named "ONTG-002-001WO-Sequence Listing.txt", which was created on Oct. 28, 2016 and is 1,636 bytes in size, are hereby incorporated by reference in their entireties.

BACKGROUND OF THE DISCLOSURE

There is a variety of pain conditions including neuropathic pain, ocular pain, and ocular inflammation.

Neuropathic pain is a complex, chronic pain state that usually is accompanied by tissue injury. With neuropathic pain, the nerve fibers themselves might be damaged, dysfunctional, or injured. These damaged nerve fibers send incorrect signals to other pain centers. The impact of a nerve fiber injury includes a change in nerve function both at the site of injury and areas around the injury. Neuropathic pain is a serious health problem that affects millions of people worldwide and occurs in as much as 7% of the general population. The management of neuropathic pain in patients is complex with an estimated 40-60% of individuals refractive to existing analgesic therapies. The aging population, the diabetes epidemic, and patients with cancer and AIDS all contribute to the prevalence of intractable neuropathic pain, highlighting the pressing need to develop novel therapeutics for this condition.

The eye is heavily innervated by sensory nerve fibers, and inflammatory, ischemic, and even neoplastic involvement of the eye and orbit can produce pain. Ophthalmic causes of eye pain include dry eyes and other forms of keratitis, acute angle-closure glaucoma, and intraocular inflammation. Keratitis sicca, or dry eye, is a very common cause of ophthalmic discomfort. These conditions are most commonly diagnosed through examination of the cornea, anterior segment, and anterior vitreous by slit lamp. Exacerbated by visual tasks that decrease blink frequency, especially work on the computer, it has various causes and results from conditions that either decrease tear production or increase tear evaporation. Dry eye is one of the characteristic features of the autoimmune Sjögren syndrome. Evidence of fluorescein or rose bengal staining, abnormal tear breakup time, or decreased Schirmer test may help confirm dry eye syndrome. Posterior segment examination with indirect ophthalmoscopy or slit-lamp biomicroscopy may reveal evidence of choroidal or retinal inflammation or posterior scleritis.

The present disclosure addresses the need of patients suffering from various pain conditions, such as neuropathic pain, ocular pain, ocular inflammation, and/or dry eye.

SUMMARY OF THE DISCLOSURE

The present disclosure provides compositions and methods for treating or ameliorating at least one symptom of neuropathic pain, ocular pain, ocular inflammation, and/or dry eye.

The present disclosure provides a composition comprising a lipidated bovine adrenal medulla peptide 8-22 (BAMS-22) peptide analog. The composition can comprise a BAMS-22 peptide, a PEG-8 linker with a Lys-Gly-Gly (KGG) spacer, and a palmitic acid membrane anchor. The BAMS-22 peptide can comprise the amino acid sequence of SEQ ID NO:1. The BAMS-22 peptide and the KGG spacer can comprise the amino acid sequence of SEQ ID NO:2. The PEG-8 linker and the palmitic acid membrane anchor can be coupled to the amino side chain group of the C-terminal lysine of the BAMS-22 peptide.

The BAMS-22 peptide can comprise at least one amino acid modification. The at least one amino acid modification can reduce or inhibit protease activity. The protease activity can be serine protease activity. The at least one amino acid modification can be at position 15 of SEQ ID NO:1. The modification at position 15 of SEQ ID NO:1 can be a M to A substitution (M15A). The at least one amino acid modification can be at position 17 of SEQ ID NO:1. The modification at position 17 of SEQ ID NO:1 can be a Y to W substitution (Y17W). The BAM8-22 peptide can comprise at least two amino acid modifications. The at least two amino acid modifications can be at positions 15 and 17 of SEQ ID NO:1. The modification at position 15 of SEQ ID NO:1 can be a M to A substitution (M15A) and the modification at position 17 of SEQ ID NO:1 can be a Y to W substitution (Y17W).

The present disclosure also provides a composition comprising a lipidated γ2-melanocyte stimulating hormone (γ2-MSH) peptide analog. The composition can comprise a γ2-MSH peptide, a PEG-8 linker, and a palmitic acid membrane anchor. The γ2-MSH peptide can comprise the amino acid sequence of SEQ ID NO:3. The PEG-8 linker and the palmitic acid membrane anchor can be coupled to the N-terminus of the γ2-MSH peptide. The γ2-MSH peptide can comprise at least one amino acid modification. The at least one amino acid modification can reduce or inhibit protease activity.

The present disclosure also provides pharmaceutical composition comprising any of the compositions of the present disclosure (e.g., lipidated BAMS-22 peptide or lipidated γ2-MSH peptide or a combination thereof) and a pharmaceutically acceptable carrier.

The present disclosure also provides a method of treating neuropathic pain in a subject in need thereof comprising administering a therapeutically effective amount of any of the compositions of the present disclosure (e.g., lipidated BAMS-22 peptide or lipidated γ2-MSH peptide or a combination thereof).

The present disclosure also provides a method of treating ocular pain in a subject in need thereof comprising administering a therapeutically effective amount of any of the compositions of the present disclosure (e.g., lipidated BAMS-22 peptide or lipidated γ2-MSH peptide or a combination thereof).

The present disclosure also provides a method of treating ocular inflammation in a subject in need thereof comprising administering a therapeutically effective amount of any of the compositions of the present disclosure (e.g., lipidated BAMS-22 peptide or lipidated γ2-MSH peptide or a combination thereof).

The present disclosure also provides a method of treating dry eye in a subject in need thereof comprising administering a therapeutically effective amount of any of the compositions of the present disclosure (e.g., lipidated BAMS-22 peptide or lipidated γ2-MSH peptide or a combination thereof).

In some embodiments, the peptide or peptide analog of the present disclosure is cyclized. For example, the BAMS-22 peptide or lipidated BAMS-22 peptide analog is cyclized. In yet another example, the γ2-MSH peptide or lipidated γ2-MSH peptide analog is cyclized.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

DETAILED DESCRIPTION OF THE DISCLOSURE

Figure 1A:
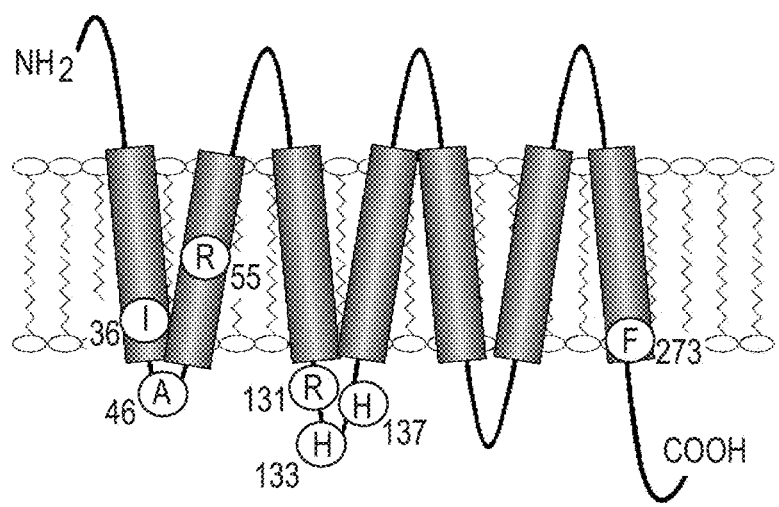
FIG. 1A is a schematic of the MrgprX1 seven transmembrane domain structure highlighting the positions of MrgprX1 missense mutations.

In one aspect, the present disclosure provides a composition comprising a lipidated BAMS-22 peptide analog.

In another aspect, the present disclosure provides a composition comprising a BAMS-22 peptide, a PEG-8 linker with a KGG spacer, and a palmitic acid membrane anchor. As used herein, the term "PEG" refers to polyethylene glycol.

In another aspect, the present disclosure provides a composition comprising a lipidated γ2-MSH peptide analog.

In another aspect, the present disclosure provides a composition comprising a γ2-MSH peptide, a PEG-8 linker, and a palmitic acid membrane anchor.

In another aspect, the present disclosure provides a method of treating neuropathic pain in a subject in need thereof comprising administering a therapeutically effective amount of any of the compositions of the present disclosure (e.g., lipidated BAMS-22 peptide or lipidated γ2-MSH peptide or a combination thereof).

In another aspect, the present disclosure also provides a method of treating ocular pain in a subject in need thereof comprising administering a therapeutically effective amount of any of the compositions of the present disclosure (e.g., lipidated BAMS-22 peptide or lipidated γ2-MSH peptide or a combination thereof).

In another aspect, the present disclosure also provides a method of treating ocular inflammation in a subject in need thereof comprising administering a therapeutically effective amount of any of the compositions of the present disclosure (e.g., lipidated BAMS-22 peptide or lipidated γ2-MSH peptide or a combination thereof).

In another aspect, the present disclosure also provides a method of treating dry eye in a subject in need thereof comprising administering a therapeutically effective amount of any of the compositions of the present disclosure (e.g., lipidated BAMS-22 peptide or lipidated γ2-MSH peptide or a combination thereof).

In another aspect, the present disclosure also provides a method of detecting mutations in specific G-protein coupled receptors using any of the compositions of the present disclosure (e.g., lipidated BAMS-22 peptide or lipidated γ2-MSH peptide or a combination thereof).

As described in further detail herein, there is an unmet need for novel strategies to treat pain, in particular neuropathic pain, a disease which affects millions of people worldwide and occurs in as much as 7% of the population. The management of patients with neuropathic pain is complex, with many patients not responding to treatment or only experiencing partial relief. At the extreme, there is a substantial subpopulation with moderate to severe chronic refractory pain where there is an urgent need for more effective, long acting therapeutics.

The transmission of pain is mediated in part by primary sensory neurons of the dorsal root ganglia. Although the mediators of pain are complex, selected G protein-coupled receptors (GPCRs) have been implicated in the modulation of nociception. Recently, a group of GPCRs, the Mrgprs (also denoted Mrgpr/SNSR) were discovered in specific subsets of sensory neurons. It has been determined that mouse MrgprC11, rat MrgprC, and human MrgprX1 were three orthologous receptors that are activated by the same ligand. Stimulation of these receptors with bovine adrenal medulla 8-22 peptide (BAMS-22), a gene product of the proenkephalin A gene, results in activation of Gaq leading to increases in intracellular calcium. In mouse and rat models of neuropathic pain (chronic constriction injury and spinal nerve ligation, respectively), intrathecal administration of BAMS-22 attenuates mechanical allodynia. Importantly, BAMS-22 administration did not affect baseline nociception, thereby not compromising protective physiological pain. One of the substantial limitations of using endogenous peptides as therapeutics is their short half-life. In the above mentioned neuropathic pain models, the effect of intrathecal BAMS-22 administration was transient with a short window of therapeutic efficacy.

The present disclosure provides long-acting, high potency, stable peptides as modulators of GPCRs. The present disclosure provides modified endogenous bovine adrenal medulla peptide 8-22 (BAMS-22) and modified endogenous γ2-melanocyte stimulating hormone (γ2-MSH) to generate higher potency analogs that anchor in the cell membrane and provide local activity. Specifically, the compositions of the present disclosure include, but are not limited to, BAMS-22 and γ2-MSH lipid modified to include a lipid-anchor. Additionally, the amino acids in these compositions of the present disclosure can be further modified to enhance protease resistance.

Figure 1B:
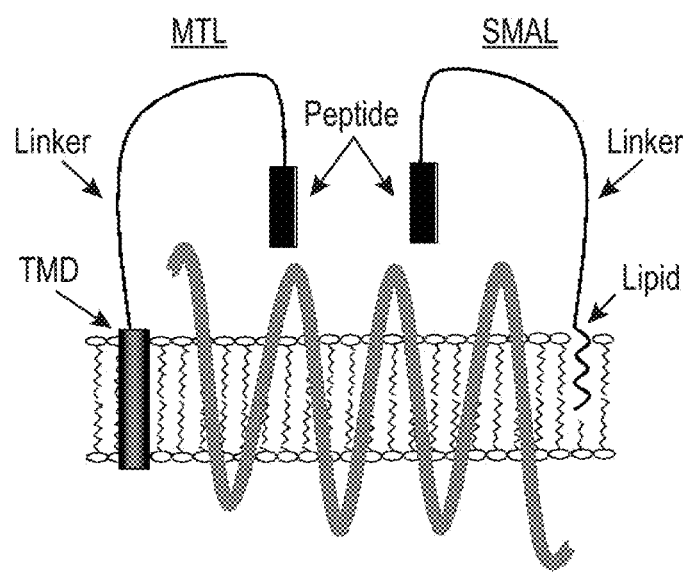
FIG. 1B is a schematic representation of an MTL and a SMAL in relation to a GPCR.

The present disclosure also provides methods of producing the compositions provided herein. One of the advantages of the methods of the present disclosure is starting with a recombinant system that allows for rapid optimization of a peptide. In Step 1, a membrane tethered ligand (MTL) is created using a peptide sequence known to activate a GPCR of interest. An alanine scan is performed to determine amino acid positions amenable to substitution. Optimized variants are created by altering selected amino acid positions to enable protease resistance while maintaining activity. Once an optimized ligand is identified, in Step 2 this peptide is incorporated as a component of a synthetic membrane anchored ligand (SMAL) which enables delivery as a soluble molecule. The components of the SMAL (peptide-linker-anchor) can each be varied to further fine tune pharmacological activity, as needed. The left side of FIG. 1B shows a MTL-GPCR interaction. An MTL cDNA construct encodes a single protein comprised of three domains: (i) a peptide ligand, (ii) a flexible protein linker which includes an epitope tag (enabling detection of expression), and (iii) a transmembrane domain (TMD). The right side of FIG. 1B shows a SMAL-GPCR interaction. A SMAL includes the following domains (i) a peptide ligand, (ii) a synthetic linker (e.g. PEG8), and (iii) a lipid anchor (e.g. palmitic acid) which inserts into the membrane where it is locally applied (e.g. into the intrathecal space).

This approach is utilized to enhance the stability and activity of the compositions of the present disclosure. This approach also provides additional advantages.

The recombinant nature of MTLs enables efficient generation of candidate peptides (without the need for synthesis and purification). The proximity of membrane anchored ligands to cognate receptors enhances 'effective local concentration', a major advantage in generating high affinity ligands. The recombinant MTL system enables the generation and characterization of protease resistant peptides. SMAL stability can be further enhanced through the introduction of unnatural amino acids that are tolerated at selected positions. The cassette configuration of SMALs (peptide-linker-anchor) offers multiple opportunities (e.g. modifying peptide, linker length, and/or nature of membrane anchor) to fine tune compound function (e.g. efficacy, potency, half-life, protease resistance). The chronic constriction injury model provides a rapid readout of therapeutic efficacy in vivo. Combined with the modular MTL/SMAL system, this allows for a rapid identification of highly potent compositions.

The peptide or peptide analog described herein can be cyclized. Such "cyclic peptides" have intramolecular links which connect two amino acids. Cyclic peptides are often resistant to proteolytic degradation and are thus good candidates for oral administration. The intramolecular linkage may encompass intermediate linkage groups or may involve direct covalent bonding between amino acid residues. In some embodiments, the N-terminal and C-terminal amino acids are linked. In other embodiments, one or more internal amino acids participate in the cyclization. Cyclization can be, for example, but not by way of limitation, via a disulfide bond between two cysteine residues or via an amide linkage. The cysteine residues can be native or artificially introduced to the peptide. For example, cysteine residues can be introduced at the amino-terminus and/or carboxy-terminus and/or internally such that the peptide to be cyclized. Alternatively, a cyclic peptide can be obtained by forming an amide linkage. For example, an amide linkage can be achieved by the following protocol: (1) an allyl protected amino acid, such as aspartate, glutamate, asparagine or glutamine, can be incorporated into the peptide as the first amino acid; (2) then the remaining amino acids are coupled on to form a cycle. Other methods known in the art may be employed to cyclize peptides of the disclosure. For example, cyclic peptides may be formed via side-chain azide-alkyne 1,3-dipolar cycloaddition (Cantel et al. *J. Org. Chem.*, 73 (15), 5663-5674, 2008, incorporated herein by reference). Cyclization of peptides may also be achieved, e.g., by the methods disclosed in U.S. Pat. Nos. 5,596,078; 4,033,940; 4,216,141; 4,271,068; 5,726,287; 5,922,680; 5,990,273; 6,242,565; and Scott et al. PNAS. 1999. vol. 96 no. 24 P. 13638-13643, which are all incorporated herein by reference. In some embodiments, the intramolecular link is a disulfide bond mimic or disulfide bond mimetic which preserves the structure that would be otherwise be created by a disulfide bond.

In one embodiment, the BAMS-22 peptide or analog thereof is cyclized. In one embodiment, the γ2-MSH peptide or analog thereof is cyclized.

The Mas-related G protein-coupled receptor X1 (MrgprX1) is a human GPCR expressed in dorsal root ganglia (DRG) neurons (Dong et al., *Cell* 106:619-32, 2001; Lembo et al., *Nat Neurosci* 5:201-9, 2002). The endogenous ligands bovine adrenal medulla peptide 8-22 (BAM8-22) and γ2-melanocyte stimulating hormone (γ2-MSH) activate this receptor and trigger $G\alpha_q$ mediated signaling (Lembo et al., 2002; Solinski et al., *Pharmacol Rev* 66:570-597, 2014; Tatemoto et al., *Biochem Biophys Res Commun* 349:1322-8, 2006). Existing literature suggests that in mouse models, receptors in the Mrgpr family modulate nociception and pruriception in vivo (Guan et al., *Proc Natl Acad Sci USA* 107:15933-8, 2010; Liu et al., *Cell* 139:1353-65, 2009; Solinski et al., 2014). A recent report showed that in humans, BAM8-22 produces itching sensations through a histamine-independent pathway (Sikand et al., *J Neurosci* 31:7563-7, 2011). Despite these studies, there still remain many unanswered questions regarding the precise role of MrgprX1 in mediating somatosensory signals. Analysis of the coding region of the MrgprX1 gene revealed genetic variation among humans (NHLBI GO Exome Sequencing Project), shown in FIG. 1A and Table 1.

Naturally occurring variants of GPCRs have proved helpful in understanding differences in susceptibility to disease. The present disclosure provides compositions and methods for detecting MrgprX1 missense mutations and determining the extent to which these MrgprX1 missense mutations alter the pharmacological response of MrgprX1, for example to the endogenous ligand BAMS-22.

A series of novel agonists (FIG. 1B) were developed to enable more detailed characterization of signaling differences among MrgprX1 variants. Lipidated constructs were generated corresponding to the two active MrgprX1 MTLs. Guided by the MTL results, PEG8 and palmitic acid were covalently attached to the C-terminus of BAMS-22 and the N terminus of γ2-MSH to generate corresponding SMALs (Table 2). Methods of generating lapidated peptides are disclosed in US20160052982, the contents of which are incorporated herein by reference.

a lipid moiety, yields potent, soluble ligands that anchor to the cell surface and activate the corresponding GPCR (Doyle et al., *J Biol Chem* 289:13385-96, 2014; Fortin et al., 2011). Potential advantages of such ligands include increased potency and prolonged stability (Zhang and Bulaj, *Curr Med Chem* 19:1602-18, 2012).

In the present disclosure, this developed panel of ligands is used to characterize a series of MrgprX1 missense mutations with an allele frequency exceeding 0.1% (Table 1).

TABLE 1

Allele frequencies of MgprX1 missense variants.
All data were collected from the NHLBI GO
ESP Exome Variant Server.

| Variant | dbSNP Reference ID | EA Frequency | AA Frequency |
|---|---|---|---|
| I36V | rs11024885 | 0.63% | 10.17% |
| A46T | rs78179510 | 17.69% | 19.24% |
| R55L | rs55954376 | 0.01% | 3.42% |
| R131S | rs111448117 | 1.19% | 0.23% |
| H133R | rs140351170 | 0.33% | 0.07% |
| H137R | rs143702818 | 0.01% | 0.41% |
| F273L | rs138263314 | 2.44% | 0.53% |

Abbreviations:
EA, European American;
AA, African American.

A schematic representation of MrgprX1 (FIG. 1A) highlights the location of each variant residue. The wild type

TABLE 2

Chemical structure of synthesized lipidated peptides.

| Peptide | Structure | Molecular Weights (Da) | |
|---|---|---|---|
| | | Calculated[a] | Observed[b] |
| Lipidated BAM8-22[c] | H₂N—VGRPEWWMDYQKRYGGGK—CO₂H (with ε-NH linker-PEG8-palmitoyl) | 2875.0 | 2872.7 |
| Lipidated γ2-MSH[d] | HN—YVMGHFRWDRFG—CO₂H (with PEG8 linker-palmitoyl on N-terminus) | 2231.2 | 2230.9 |

[a]Calculated molecular weights were estimated using GenScript (Piscataway, NJ).
[b]Observed molecular weights were determined by MALDI-TOF MS (Bruker microflex LT) in a positive reflectron mode using α-cyano-4-hydroxy cinnamic acid as the matrix.
[c]Lipidated BAM8-22 is comprised of BAM8-22 and a GGK spacer coupled to a PEG8 linker domain and palmitic acid.
Note
that the linker-lipid modification is on the amino side chain group (N$^ε$) of the C-terminal lysine.
[d]Lipidated γ2-MSH is comprised
of γ2-MSH coupled to a PEG8 linker domain and palmitic acid.
Note
that the linker-lipid modification is on the N terminus of the peptide. BAM8-22 (VGRPEWWMDYQKRYG) (SEQ ID NO: 1); BAM8-22 with GGK Spacer (VGRPEWWMDYQKRYGGGK) (SEQ ID NO: 2); γ2-MSH (YVMGHFRWDRFG) (SEQ ID NO: 3)

Previous work has shown that peptide ligands may be anchored to the cell surface using recombinant DNA technology. Such membrane-tethered ligands (MTLs) provide a complementary tool to explore GPCR function (Fortin et al., *PLoS One* 6:e24693, 2011; Fortin et al., *Proc Natl Acad Sci USA* 106:8049-54, 2009; Harwood et al., *Mol Pharmacol* 83:814-21, 2013). Conversion of these recombinant ligands into synthetic membrane anchored ligands (SMALs), in which a peptide is covalently coupled to a flexible linker and a lipid moiety, yields potent, soluble ligands that anchor to amino acids in positions where sequence variations occur are indicated by the single letter code. The present compositions and methods demonstrate that two mutations in MrgprX1, R131S and H133R, alter receptor mediated signaling, resulting in loss and gain of function respectively. These variants may modify susceptibility to histamine-independent itch and/or nociception.

Figure 2:
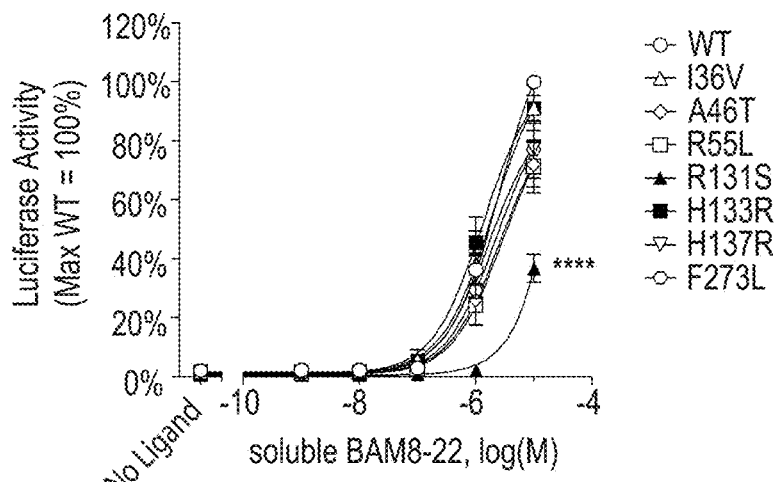
FIG. 2 is a graph showing that the R131S MrgprX1 variant demonstrates reduced endogenous ligand mediated signaling.

Initial analysis of naturally occurring MrgprX1 variants with the endogenous ligand BAMS-22 identified R131S as a potential loss-of-function mutation (FIG. 2). To further investigate ligand-mediated signaling of this variant as well as other receptor mutants, MTL and SMAL analogs of BAMS-22 and γ2-MSH were generated. In addition to confirming the loss of function resulting from the R131S mutation, use of these recombinant and synthetic ligands revealed that the H133R substitution conferred a ligand-dependent gain of function phenotype (FIGS. 4A-4B and 5A-5B). Defining how missense mutations in this receptor alter pharmacological function is an important first step towards understanding the potential role of natural variants in altering somatosensation and/or the response to drugs targeting MrgprX1 in vivo.

There are multiple mechanisms through which missense mutations may affect GPCR function. Some variants affect the active/inactive state equilibrium and may in turn have systematic effects on ligand-mediated signaling (Beinborn et al., *Mol Pharmacol* 65:753-60, 2004; Kopin et al., *Proc Natl Acad Sci USA* 100:5525-30, 2003; Samama et al., *J Biol Chem* 268:4625-4636, 1993). Other mutations alter ligand interaction with the receptor, either directly or indirectly through changes in receptor tertiary structure. (Bond et al., *Proc Natl Acad Sci USA* 95:9608-13, 1998; Fortin et al., *Mol Pharmacol* 78:837-45, 2010).

Figure 7A:
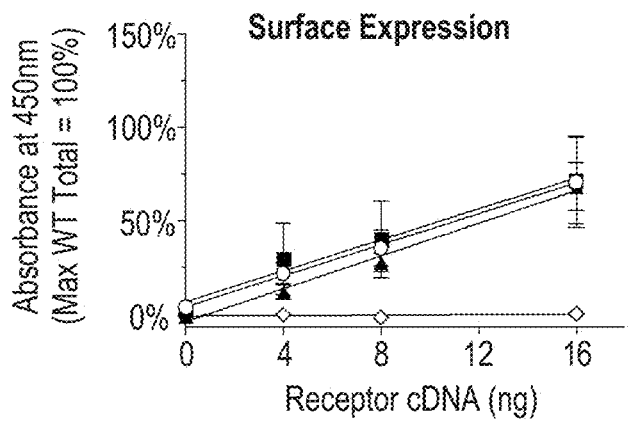
FIG. 7A is a graph showing that both the R131S and H133R variants exhibit levels of surface expression comparable to wild-type MrgprX1.
Figure 7B:
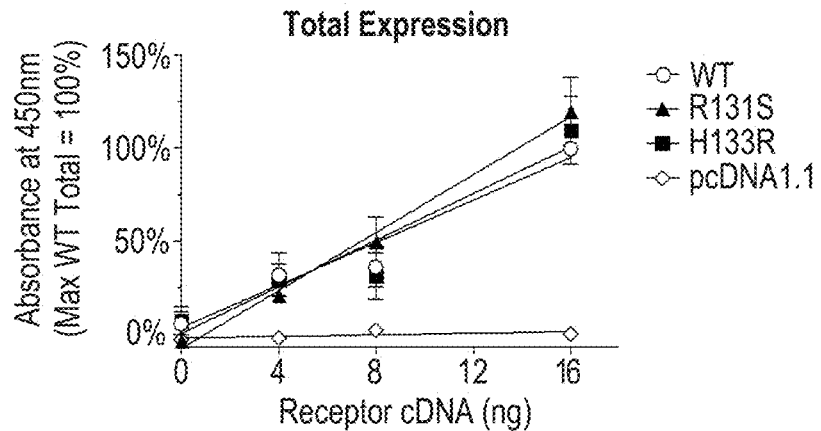
FIG. 7B is a graph showing that both the R131S and H133R variants exhibit levels of total expression comparable to wild-type MrgprX1.

The present disclosure provides that the R131S mutation decreases both ligand-mediated and ligand-independent (basal) activity of MrgprX1. These properties place it in the former group of mutations. Notably, these differences in receptor activity levels cannot be explained by changes in receptor expression (FIGS. 7A-7B). The location of residue R131 in the second intracellular loop, a domain that has been established as important in G protein binding (Hu et al., *Nat Chem Biol* 6:541-8, 2010), demonstrates that this mutation could be affecting the ability of MrgprX1 to interact with G proteins and/or shift MrgprX1 from the active to the inactive state.

The H133R mutation does not affect basal activity and slightly increases the efficacy of a subset of ligands (i.e. tethered and lipidated γ2-MSH but not tethered or lipidated BAMS-22). This demonstrates that H133R is not a systematic modulator and therefore belongs to the latter group of mutations (as described above). Like with R131S, these changes in ligand-mediated receptor activity are not accompanied by changes in receptor expression. Given its location in the second intracellular loop, H133R may represent a mutation that impacts the ligand-receptor interaction indirectly (e.g. by slightly altering the orientation of residues that interact with the ligand).

The purported role of MrgprX1 in mediating pain and somatosensation, in particular histamine-independent itch (Bader et al., *Pharmacol Rev* 66:1080-1105, 2014; Sikand et al., 2011; Solinski et al., 2014), indicates that the unique signaling properties of the R131S and H133R variants may have important implications for the development and use of therapeutics targeting this receptor. Missense variants have also proven important in understanding differences in somatosensation previously. For example, the N40D mutation in the human μ-opioid receptor (hMOR) may alter susceptibility to pain (Lötsch and Geisslinger, *Trends Mol Med* 11:82-9, 2005) and pruritus (Tsai et al., *Acta Anaesthesiol Scand* 54:1265-1269, 2010). Similarly, missense mutations in the sodium channel $Na_v1.7$ have been linked to pain-related disorders (Drenth and Waxman, *J Clin Invest* 117:3603-9, 2007; Fertleman et al., *Neuron* 52:767-74, 2006) and altered pain perception (Reimann et al., *Proc Natl Acad Sci USA* 107:5148-53, 2010).

The possibility that MrgprX1 variants may be linked to a specific phenotype highlights the need for data collection that will allow for matching of the MrgprX1 genotype with sensitivity to MrgprX1-mediated somatosensation. This should be feasible particularly with the R131S variant, which has an allele frequency of greater than 1%. Future studies may reveal that mutations such as R131S are linked to decreased nociception or pruritus. Extending beyond the coding region of the gene, variations in upstream regulatory sequences may also play a role in altering susceptibility to histamine-independent itch by altering MrgprX1 expression (Wray, *Nat Rev Genet* 8:206-16, 2007).

The compositions of the present disclosure provide powerful molecular probes to explore pharmacological differences between receptor variants. As illustrated, such modified peptide ligands (MTLs and their lapidated counterparts) exhibit enhanced effective concentration and thus provide experimental tools that facilitate the pharmacological characterization of GPCRs. In addition, MTLs can be expressed as transgenic constructs enabling exploration of corresponding receptor function in vivo (Harwood et al., *J Exp Biol* 217:4091-8, 2014). Complementing such recombinant constructs, lipidated peptides provide additional tools which can be applied in vivo to probe receptor function and validate potential therapeutic targets (Doyle et al., 2014). Notably, activity of tethered γ2-MSH and tethered BAMS-22 are recapitulated with their lipidated analogs, providing further support that MTLs are useful in predicting the pharmacological properties of corresponding lipidated peptides.

Taken together, the compositions and methods of the present disclosure demonstrate how naturally occurring missense variants may markedly alter the pharmacological properties of a GPCR. In addition, the compositions and methods of the present disclosure exemplify how MTLs and SMALs provide complementary tools to differentiate receptor variants that are systematic modulators from mutations that preferentially affect a subset of receptor agonists. As with a growing number of GPCRs (Rana et al., *Annu Rev Pharmacol Toxicol* 41:593-624, 2001; Thompson et al., *Methods Mol Blot* 1175:153-87, 2014), MrgprX1 receptor variants display important differences in both basal and ligand-induced signaling that may contribute to somatosensory variability in the human population.

Administration of the Compositions

The therapeutically effective amount of a composition according to this disclosure can vary within wide limits and may be determined in a manner known in the art. For example, the composition can be dosed according to body weight. Such dosage will be adjusted to the individual requirements in each particular case including the specific compound(s) being administered, the route of administration, the condition being treated, as well as the patient being treated. In another embodiment, the drug can be administered by fixed doses, e.g., dose not adjusted according to body weight. In general, in the case of oral or parenteral administration to adult humans, a daily dosage of from about 0.5 mg to about 1000 mg should be appropriate, although the upper limit may be exceeded when indicated. The dosage can be from about 5 mg to about 500 mg per day, e.g., about 5 mg to about 400 mg, about 5 mg to about 300 mg, about 5 mg to about 200 mg. The daily dosage can be administered as a single dose or in divided doses, or for parenteral administration it may be given as continuous infusion.

A therapeutically effective amount of a composition is that which provides an objectively identifiable improvement as noted by the clinician or other qualified observer.

The pharmaceutical compositions can be included in a container, pack, or dispenser together with instructions for administration. The compositions described herein can be administered orally, nasally, transdermally, pulmonary, inhalationally, buccally, sublingually, intraperitoneally, subcutaneously, intramuscularly, intravenously, rectally, intrapleurally, intrathecally, or parenterally. In one embodiment, the compound is administered orally. One skilled in the art will recognize the advantages of certain routes of administration.

The dosage regimen utilizing the compositions described herein is selected in accordance with a variety of factors including species, ethnicity, age, weight, sex and medical condition of the patient; the severity of the condition to be treated; the route of administration; the renal and hepatic function of the patient; and the particular composition employed. An ordinarily skilled physician or veterinarian can readily determine and prescribe the effective amount of the drug required to prevent, counter, or arrest the progress of the condition.

Techniques for formulation and administration of the disclosed compositions of the disclosure can be found in *Remington: the Science and Practice of Pharmacy, 19th* edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Methods of Treatment

The compositions described herein can be used to treat a variety of conditions including neuropathic pain, ocular pain, ocular inflammation, and dry eye.

In one aspect, the present disclosure provides a method of treating neuropathic pain with the compositions described herein. Neuropathic pain according to the present disclosure is a pain initiated or caused by a primary lesion or dysfunction in the nervous system. Neuropathic pain according to the present disclosure could be divided into "peripheral" (originating in the peripheral nervous system) and "central" (originating in the brain or spinal cord). For example, neuropathic pain syndromes include postherpetic neuralgia (caused by Herpes Zoster), root avulsions, painful traumatic mononeuropathy, painful polyneuropathy (particularly due to diabetes), central pain syndromes (potentially caused by virtually any lesion at any level of the nervous system), postsurgical pain syndromes (e.g., post mastectomy syndrome, post thoracotomy syndrome, or phantom pain), and complex regional pain syndrome (e.g., reflex sympathetic dystrophy or causalgia).

Neuropathic pain have typical symptoms like dysesthesias (spontaneous or evoked burning pain, often with a superimposed lancinating component), but the pain may also be deep and aching. Other sensations like hyperesthesia, hyperalgesia, allodynia (pain due to a normoxious stimulus), and hyperpathia (particularly unpleasant, exaggerated pain response) may also occur. The compositions of the present disclosure can be administered to ameliorate at least one of these symptoms.

Current therapy for neuropathic pain aims only at reducing symptoms, generally by suppressing neuronal activity. Thus treatment options, e.g., non-steroidal anti-inflammatory drugs (NSAIDS), antidepressants, anticonvulsants, baclofen, neuromodulation modalities, or opiates, predominantly alleviate symptoms via nonspecific reduction of neuronal hyperexcitability rather than targeting the specific etiologies. The compositions of the present disclosure can be administered in combination with the current therapy for treating neuropathic pain. For example, the compositions of the present disclosure can be administered in combination with an NSAID, an antidepressant, an anticonvulsant, baclofen, a neuromodulation modality, or an opiate for treating neuropathic pain.

In another aspect, the present disclosure provides a method of treating ocular pain with the compositions described herein. Ocular pain can be co-incident with a number of conditions, including but not limited to trauma due to accidental or surgical injury, uveitis, dry eye, and diabetic neuropathy. The standard of care for treatment of ocular pain is typically either topically administered NSAIDs, or orally administered analgesic agents, such as NSAIDS or opioids like hydrocodone. In some embodiments, the compositions of the present disclosure can be administered in combination with an NSAID or opioid for treating ocular pain.

In another aspect, the present disclosure provides a method of treating ocular inflammation with the compositions descried herein. Ocular inflammation can be caused by a microbial infection of the eye. Such infection may be fungal, viral or bacterial. Current therapies for treating ocular inflammation include locally administered anti-cytokine or anti-inflammatory agents. In some embodiments, the compositions of the present disclosure can be administered in combination with an anti-cytokine or anti-inflammatory agent for treating ocular inflammation.

The compositions described herein can also be used to treat dry eye. Dry eye is primarily caused by the break-down of the pre-ocular tear film which results in dehydration of the exposed outer surface. Without wishing to be bound by theory, there is a strong rationale that ocular inflammation as a result of pro-inflammatory cytokines and growth factors plays a major role in the underlying causes of dry eye. As such, locally administered anti-cytokine or anti-inflammatory agents are often used in the treatment of dry eye. In some embodiments, the compositions of the present disclosure can be administered in combination with an anti-cytokine or anti-inflammatory agent for treating dry eye.

With respect to combination therapies involving a first therapeutic agent (e.g., a composition of the present disclosure) and a second therapeutic agent (e.g., an anti-inflammatory agent, an opioid, an NSAID, or an antidepressant), the first therapeutic agent can be administered concurrently with the second therapeutic agent; the first therapeutic agent can be administered before the second therapeutic agent; or the first therapeutic agent can be administered after the second therapeutic agent. The administrations of the first and second therapeutic agents can be separated by minutes or hours, e.g., one hour, two hours, three hours, four hours, five hours, or six hours.

Definitions

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein. It is to be understood that the terminology used herein is for the purpose of describing particular embodiments only, and is not intended to be limiting.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and amino acid mimetic). Peptides may be naturally occurring, synthetically produced, or recombinantly expressed. Peptides may also comprise additional groups modifying the amino acid chain, for example, functional groups added via post-translational modification. Examples of post-translation modifications include, but are not limited to, acetylation, alkylation (including methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxyl terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). The term peptide also includes modifications, such as but not limited to those described above, of amino acids falling between the amino and carboxy termini. The term peptide can also include peptides modified to include one or more detectable labels.

The phrase "amino acid residue" as used herein refers to an amino acid that is incorporated into a peptide by an amide bond or an amide bond mimetic.

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

As used herein, the terms "treat," "treating," "treatment," and the like refer to reducing or ameliorating a disorder and/or a symptom associated therewith. It will be appreciated that, although not precluded, treating a disorder or condition does not require that the disorder or symptom associated therewith be completely eliminated. The terms "treat," "treating," or "treatment," do not include prevention.

As used herein, a "subject" can be any mammal, e.g., a human, a non-human primate, mouse, rat, dog, cat, cow, horse, pig, sheep, goat, camel. In a preferred embodiment, the subject is a human.

As used herein, a "subject in need thereof" is a subject having neuropathic pain, ocular pain, ocular inflammation, or dry eye.

As used herein, the singular forms "a," "an" and "the" include plural referents unless the context clearly dictates otherwise. Thus, for example, reference to "a solvent" includes a combination of two or more such solvents, reference to "a peptide" includes one or more peptides, or mixtures of peptides, reference to "a drug" includes one or more drugs, reference to "a device" includes one or more devices, and the like. Unless specifically stated or obvious from context, as used herein, the term "or" is understood to be inclusive and covers both "or" and "and".

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or obvious from context, as used herein, the term "about" is understood as within a range of normal tolerance in the art, for example within 2 standard deviations of the mean. About can be also be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

EXAMPLES

Example 1

Materials and Methods
Generation of Receptor cDNA Constructs

The MrgprX1 cDNA, in pcDNA 3.1, was generously provided by Dr. Xinzhong Dong (Johns Hopkins University School of Medicine, Baltimore, Md.). The construct was subcloned into pcDNA1.1 (Invitrogen). Naturally occurring missense mutations were chosen using data from the NHLBI GO ESP Exome Variant Server [Exome Variant Server, NHLBI Exome Sequencing Project (ESP), Seattle, Wash. (world wide web address at evs.gs.washington.edu/EVS/)]. Oligonucleotide-directed site-specific mutagenesis (Doyle et al., *J Lipid Res* 54:823-30, 2013; Fortin et al., *Proc Natl Acad Sci USA* 106:8049-54, 2009) was used to generate the receptor variants and corresponding epitope-tagged versions (where a hemagglutinin (HA) epitope tag was inserted immediately following the initiator methionine). Forward and reverse DNA sequencing confirmed the correct nucleotide sequences for each construct.

Generation of Recombinant Membrane Tethered Ligands (MTLs)

A Membrane Tethered Ligand (MTL) is a cDNA-encoded protein consisting of a peptide ligand fused to a transmembrane domain via a flexible linker region. Type I MTLs include a type I transmembrane domain, which orients the construct such that the N terminus of the ligand is extracellular. Conversely, type II MTLs result in an extracellular C terminus (Chou and Elrod, *Proteins* 34:137-53, 1999; Harwood et al., *Mol Pharmacol* 83:814-21, 2013). Corresponding DNA templates were used from previously published tethered exendin (type I) and tethered chemerin (type II) constructs (Doyle et al., *J Blot Chem* 289:13385-96, 2014; Fortin et al., 2009). DNA sequences corresponding to the peptide ligands were each sequentially replaced with those encoding BAMS-22 (VGRPEWWMDYQKRYG) (SEQ ID NO:1) and γ2-MSH (YVMGHFRWDRFG) (SEQ ID NO:3) (Lembo et al., 2002) using oligonucleotide-directed site-specific mutagenesis, producing both type I and type II MTLs for each peptide (Fortin et al., 2009; Harwood et al., 2013).

Generation of Synthetic Membrane Anchored Ligands (SMAL) Constructs

Reagents for peptide synthesis were purchased from Chem-Impex (Wood Dale, Ill.). N-Fmoc-PEG8-propionic acid, and palmitic acid were obtained from AAPPTec (Louisville, Ky.) and Sigma-Aldrich (St. Louis, Mo.) respectively. Peptides were assembled on 4-hydroxymethyl phenylacetamidomethyl (PAM) resin using the in situ neutralization protocol for N-Boc chemistry with 2-(1H-benzotriazol-1-yl)-1,1,3,3-tetramethyluronium hexafluorophosphate (HBTU) as the activating agent on a 0.25 mmol scale (Schnölzer et al., *Int J Pept Res Ther* 13:31-44, 2007). Peptide coupling reactions were carried out with a 4-fold excess of the protected amino acid (1 mmol). A GGK peptide spacer was added to the C terminus of BAM8-22 to enable coupling of the PEG8 linker.

After completion of the desired peptide sequence, coupling of N-Fmoc-PEG8-propionic acid to the N terminus (γ2-MSH) or the C terminus (BAMS-22) preceded coupling of the lipid (palmitic acid) using standard activation procedures (Doyle et al., 2014). Peptides were cleaved from the resin by using high HF conditions (90% anhydrous HF/10% anisole at 0° C. for 1.5 h), and precipitated using cold $Et_2O$. Crude peptides were purified by reversed phase HPLC, and the purities determined by analytical HPLC [Vydac, C18, 5μ, 4 mm×250 mm] with a linear gradient of solvent B over 20 mins at a flow rate of 1 mL/min. Elution was monitored by absorbance at 230 nm. Purities of peptides ranged from 90-95%. Peptides were analytically characterized by MALDI-TOF mass spectrometry.

Transfection and Luciferase Reporter Gene Assay

A luciferase reporter-based assay was utilized as an index of receptor-mediated signaling (as in Doyle et al., 2013). Human kidney cells (HEK293), grown in Dulbecco's modified Eagle's medium (DMEM) containing 10% FBS, 100 U/ml penicillin, and 100 μg/ml streptomycin were seeded in 96-well plates and grown to 80% confluence. Using polyethylenimine (PEI, 2.0 μg/mL in serum-free DMEM), cells were transiently transfected with cDNAs encoding (a) wild type or variant MrgprX1 (3 ng/well); (b) an SRE-luciferase PEST construct (SRE5×-Luc-PEST), which includes five SRE repeats, a luciferase reporter gene, and the protein degradation sequence hPEST (Promega, catalog #E1340) (25 ng/well); and (c) a CMV-β-galactosidase construct as a control for variability in transfection efficiency (10 ng/well). In experiments that included transfection of an MTL-encoding construct, the corresponding cDNA was added to the transfection mix, at 4 ng/well or as indicated.

Twenty-four hours following transfection, cells were stimulated with soluble ligand for 4 hours (if applicable). After addition of SteadyLite reagent (PerkinElmer, Chicago, Ill.), luciferase activity of the lysate was measured using a TopCount NTX plate reader. Subsequently, 2-nitrophenyl β-D-galactopyranoside (ONPG) was added as a colorimetric substrate to enable quantification of β-galactosidase levels. After incubation with ONPG for 30 minutes, absorbance at 420 nm was measured using a SpectraMax microplate reader (Molecular Devices). Luciferase activity was normalized using the β-galactosidase activity data. Three independent experiments were performed, each with three technical replicates. Data were graphed and statistically analyzed using Graphpad Prism software.

Enzyme-Linked Immunosorbent Assay (ELISA)

An ELISA was used to assess total and surface receptor expression (as in Doyle et al., 2013). In brief, HEK293 cells were grown and seeded as above using 96-well plates pretreated with poly-L-lysine. When 80% confluent, cells were transfected with HA-tagged receptor constructs. After 24 hours, the cells were fixed with 4% paraformaldehyde in phosphate buffered saline (PBS) for 10 min. To measure total expression levels, 0.1% Triton X-100 in PBS was applied in order to permeabilize the cell membrane. To assess surface expression, treatment with Triton X-100 was omitted. Cells were washed with PBS/100 mM glycine and then incubated in PBS/20% FBS for 30 minutes in order to block nonspecific antibody binding. A horseradish peroxidase (HRP)-conjugated antibody directed against the HA epitope tag (Roche, catalog #12013819001) was diluted 1:500 and added to the cells for 3 hours. Cells were then washed 5 times with PBS. The HRP substrate BM-blue (3,3'-5,5'-tetramethylbenzidine, Roche) was added at 50 μl per well. After 30 minutes, 50 μl of 2.0 M sulfuric acid was added to each well to stop the reaction. The concentration of the colorimetric product was quantified by measuring absorbance at 450 nm using a SpectraMax microplate reader (Molecular Devices).

Data Analysis

GraphPad Prism software version 6.0 (GraphPad Software Inc., La Jolla, Calif.) was used for sigmoidal curve fitting of ligand concentration—response curves, linear regression, and statistical analysis. $EC_{50}$ and $pEC_{50}$ values were calculated for each independent experiment as an index of ligand potency. Reported values represent the mean of three independent experiments. Statistical comparisons were made by one-way analysis of variance with Dunnett's multiple comparisons test.

Example 2

Missense Mutations in MrgprX1 Result in Differing Levels of Endogenous Peptide-Mediated Signaling.

Signaling of MrgprX1 following stimulation with the endogenous peptide ligand BAM8-22 was measured using a luciferase reporter assay as described herein. Cells expressing MrgprX1 (WT or variant receptors) were stimulated for 4 hours with soluble BAMS-22. The R131S MrgprX1 variant shows reduced endogenous ligand mediated signaling (FIG. 2). HEK293 cells were transfected with cDNA encoding either wild type or variant MrgprX1, an SRE-luciferase reporter construct, and β-galactosidase. After 24 hours, cells were stimulated with soluble BAMS-22 for 4 hours. Luciferase activity was quantified and normalized relative to β-galactosidase expression. Three independent experiments were performed in triplicate, and data were expressed relative to the wild type receptor signal (maximum stimulation=100%). Results are shown as the mean±SEM. ****, p<0.0001 vs. WT (at $10^{-5}$ M). Concentration-response curves presented in FIG. 2 illustrate that six of the seven MrgprX1 variants assayed have a normal response to the ligand. However, the R131S variant exhibited lower levels of BAMS-22 mediated activity. The R131S best-fit curve is shifted to the right, suggesting a significant loss of potency. Since soluble BAMS-22 does not fully stimulate the receptors when applied at the highest tested concentration (10 μM), accurate $EC_{50}$ values could not be calculated. It should be noted that HEK293 cells transfected with an empty vector control show no activity after treatment with ligand (data not shown).

Example 3

Characterization of Novel Recombinant and Synthetic MrgprX1 Ligands.

As additional tools for structure-function studies, MTLs incorporating one of two endogenous peptide ligands for MrgprX1, BAMS-22 and γ2-MSH, were generated. The activities of MTL constructs in both orientations (type I, with an extracellular N terminus of the ligand; type II, with an extracellular C terminus) were assessed using a luciferase-based reporter assay as described herein. FIGS. 3A-3D show that Type I tethered BAMS-22 (FIG. 3A) and type II tethered γ2-MSH (FIG. 3B) are active on the WT receptor. Lipidated BAMS-22 and lipidated γ2-MSH exhibit increased potency compared to the corresponding soluble peptides (FIG. 3C and FIG. 3D, respectively). To determine MTL activity, HEK293 cells were transfected with increasing amounts of cDNA encoding either tethered BAMS-22 or tethered γ2-MSH, as well as a fixed amount of cDNA encoding wild type MrgprX1, an SRE-luciferase reporter construct, and β-galactosidase. To determine synthetic membrane anchored ligand activity, similar methodology was utilized with tether cDNA omitted. Twenty-four hours after transfection, the cells were stimulated with lipidated BAMS-22 or lipidated γ2-MSH for 4 hours. Luciferase activity was quantified and normalized relative to β-galactosidase expression. Data shown represent at least two independent experiments performed in triplicate. Results were expressed relative to the wild type receptor signal (maximum=100%) and graphed as mean±SEM.

Figure 3A:
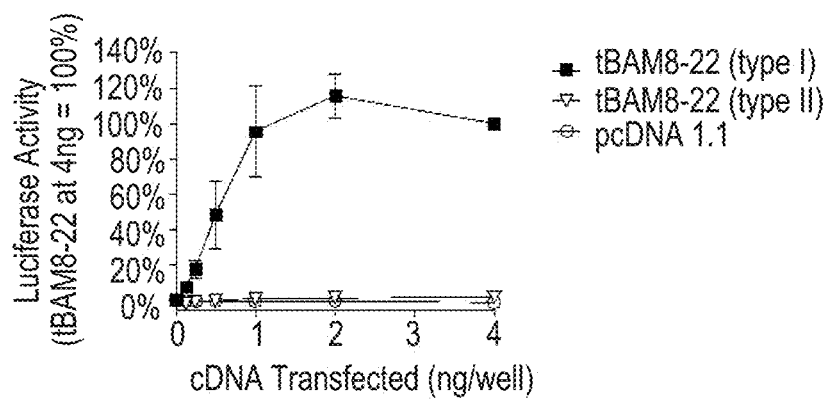
FIG. 3A is a graph showing that Type I tethered BAMS-22 is active on the WT receptor.
Figure 3B:
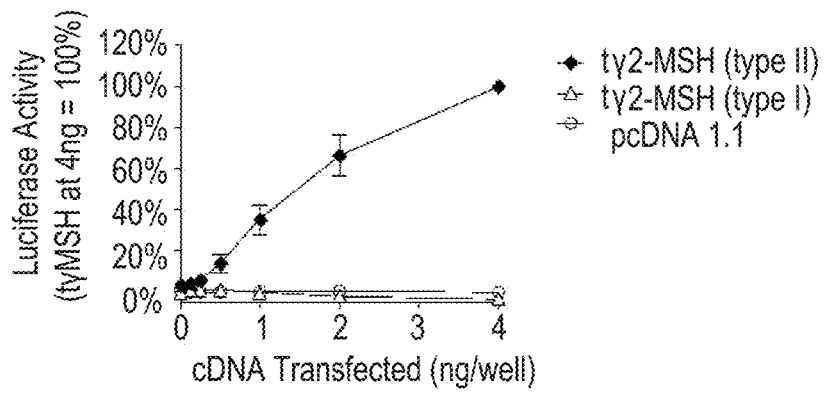
FIG. 3B is a graph showing that type II tethered γ2-MSH is active on the WT receptor.
Figure 3C:
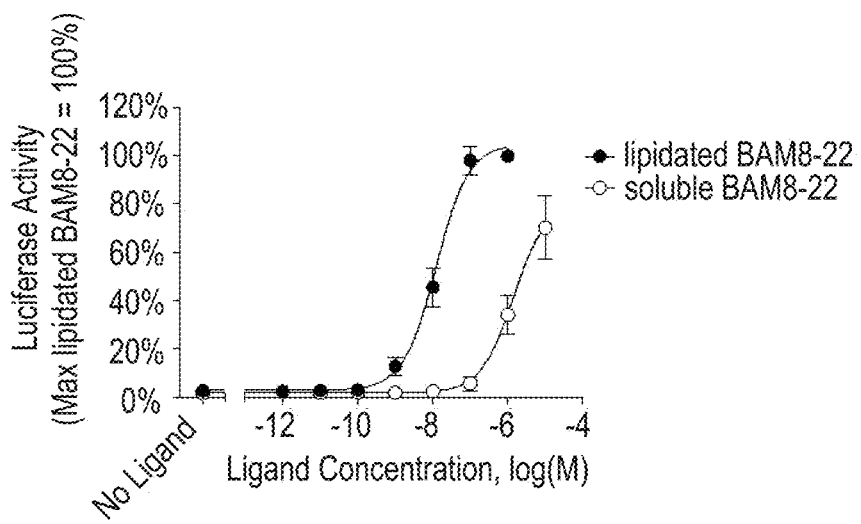
FIG. 3C is a graph showing that lipidated BAMS-22 exhibited increased potency compared to the corresponding soluble peptide.
Figure 3D:
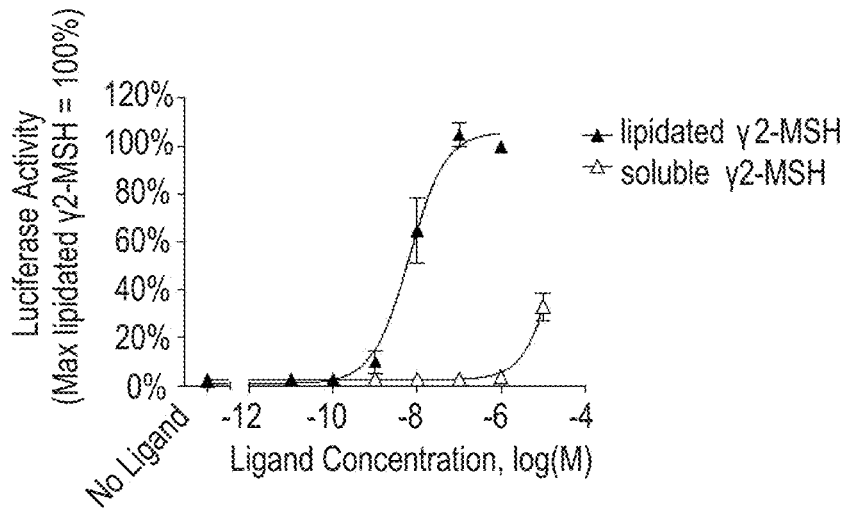
FIG. 3D is a graph showing that lipidated γ2-MSH exhibited increased potency compared to the corresponding soluble peptide.

When expressed in HEK293 cells together with MrgprX1, a subset of MTL constructs activated the receptor in a cDNA concentration-dependent manner (FIG. 3A, 3B). Active MTLs included type I tethered BAM8-22 (free extracellular N terminus) and type II tethered γ2-MSH (free extracellular C terminus). These constructs were therefore used in subsequent experiments.

Using synthetic membrane anchored ligands (SMALs) which integrate into the cellular membrane via a lipid moiety (Doyle et al., 2014; Fortin et al., *PLoS One* 6:e24693, 2011), recapitulating the activity of recombinant MTLs was attempted. Lipidated constructs were generated corresponding to the two active MrgprX1 MTLs. Guided by the MTL results, PEG8 and palmitic acid were covalently attached to the C-terminus of BAMS-22 and the N terminus of γ2-MSH to generate corresponding SMALs (Table 2). When compared to the endogenous soluble form, both lipidated BAMS-22 and lipidated γ2-MSH displayed significantly increased potency (FIGS. 3C, 3D).

In a parallel set of experiments (data not shown), signaling levels at saturating concentrations of the four novel MrgprX1 ligands were assessed at the WT receptor. Tethered BAMS-22, tethered γ2-MSH, and lipidated γ2-MSH signaling represented 38.4±5.4, 12.9±2.0, and 67.9%±2.4 (mean±SEM) of maximum lipidated BAMS-22 signaling (at $10^{-7}$ M), respectively.

Example 4

Select MrgprX1 Missense Mutations Result in Altered Ligand Mediated Signaling.

Figure 4A:
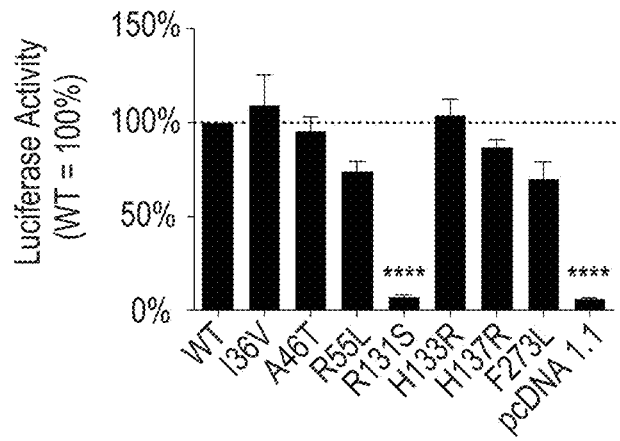
FIG. 4A is a graph showing that the R131S variant displays negligible signaling levels with tethered BAMS-22.
Figure 4B:
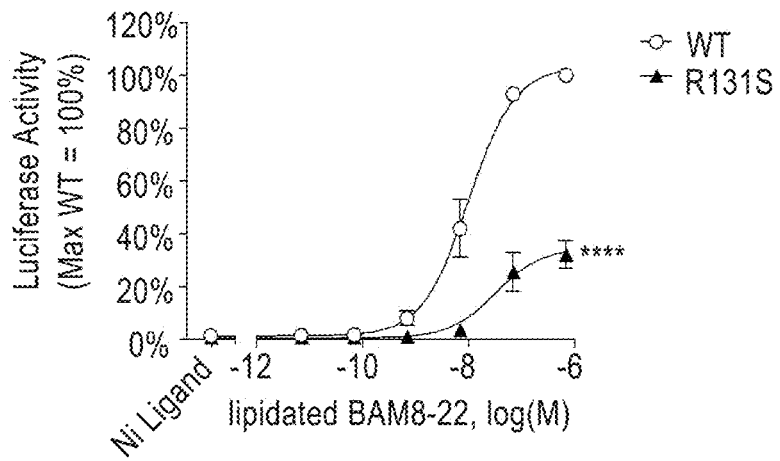
FIG. 4B is a graph showing that the R131S variant displays reduced signaling with lipidated BAMS-22.

The activity of tethered and lipidated BAMS-22 at each of the seven MrgprX1 variants was assessed (FIGS. 4A-4B). The R131S variant displays negligible signaling levels with tethered BAMS-22 (FIG. 4A) as well as reduced signaling with lipidated BAMS-22 (FIG. 4B). To measure MTL activity, HEK293 cells were transfected with cDNAs encoding tethered BAMS-22, either wild type or variant MrgprX1, an SRE-luciferase reporter construct, and β-galactosidase. The empty vector, pcDNA1.1, was transfected instead of receptor cDNA as a control. To measure synthetic membrane anchored ligand activity, a similar methodology was utilized with the tether cDNA omitted. Cells were stimulated 24 hours after transfection with lipidated BAMS-22 for four hours. Luciferase activity was quantified and normalized relative to 3-galactosidase expression. For each receptor, three independent experiments were performed in triplicate. Data are expressed relative to the maximum signal achieved at the wild type receptor. Results are shown as the mean±SEM. ****, $p<0.0001$ variant receptor vs. WT (at $10^{-6}$ M in FIG. 4B). All variants except R131S are significantly different from pcDNA1.1 ($p<0.05$).

Following stimulation with either the recombinant or the synthetic BAMS-22 analog, the R131S variant consistently displays attenuated levels of signaling. In addition to decreased efficacy, a statistical analysis of calculated $EC_{50}$ values for all seven variants suggests that only the R131S mutation significantly decreases the potency and efficacy of lipidated BAMS-22 (Table 3).

TABLE 3

Comparison of signaling induced by lipidated BAM8-22 at selected MrgprX1 variants.

| Variant | $EC_{50}$ (nM) | $pEC_{50}{}^a$ | Curve Maximum$^{a,b}$ |
|---|---|---|---|
| WT | 12.0 | 7.92 ± 0.065 | 101.3% ± 2.7 |
| I36V | 9.3 | 8.03 ± 0.12 | 108.9% ± 5.4 |
| A46T | 9.5 | 8.02 ± 0.112 | 111.6% ± 5.2 |
| R55L | 10.2 | 7.99 ± 0.142 | 107.5% ± 6.4 |
| R131S | 57.1 | 7.24 ± 0.117**** | 40.4% ± 2.5**** |
| H133R | 8.6 | 8.06 ± 0.103 | 110.2% ± 4.6 |
| H137R | 7.9 | 8.10 ± 0.089 | 109.2% ± 4.0 |
| F273L | 12.1 | 7.92 ± 0.076 | 95.9% ± 3.1 |

$^a$shown as mean ± SEM
$^b$curve maxima are extrapolated from the best-fit curve. Luciferase signal at the WT receptor achieved at $10^{-6}$ M lipidated BAM8-22 is defined as 100%.
****$p < 0.0001$ (vs. WT)

Figure 5A:
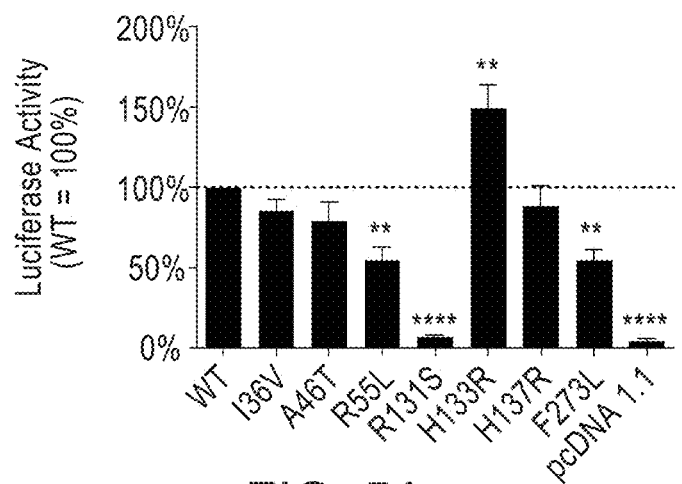
FIG. 5A is a graph showing that when stimulated with tethered γ2-MSH, the R131S and H133R variants exhibit decreased signaling levels compared to the wild type receptor.
Figure 5B:
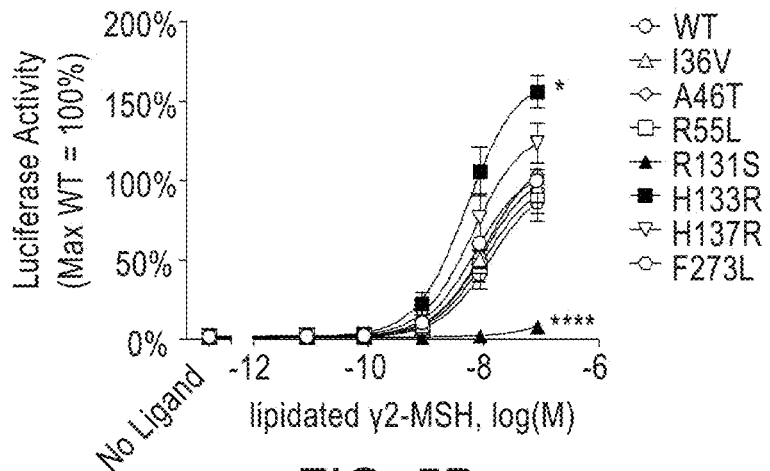
FIG. 5B is a graph showing that when stimulated with lipidated γ2-MSH, the R131S and H133R variants exhibit increased signaling levels compared to the wild type receptor.

The R131S variant also displays decreased ligand-mediated signaling with either tethered or lipidated γ2-MSH (FIGS. 5A-5B). When stimulated with tethered (FIG. 5A) or lipidated (FIG. 5B) γ2-MSH, the R131S and H133R variants exhibit decreased and increased signaling levels compared to the wild type receptor, respectively. To measure MTL activity, HEK293 cells were transfected with cDNAs encoding tethered γ2-MSH, either wild type or variant MrgprX1, an SRE-luciferase reporter construct, and β-galactosidase. The empty vector, pcDNA1.1, was transfected instead of receptor cDNA as a control for background signaling. To measure synthetic membrane anchored ligand activity, the tether cDNA was omitted. Cells were stimulated 24 hours after transfection with lipidated γ2-MSH for four hours. Luciferase activity was quantified and normalized relative to β-galactosidase expression. For each receptor, three independent experiments were performed in triplicate. Data are expressed relative to the maximum signal achieved at the wild type receptor. Results are shown as the mean±SEM. *, $p<0.05$; , $p<0.01$; **, $p<0.0001$ vs. WT (at $10^{-7}$ M in FIG. 5B). All variants except R131S are significantly different from pcDNA1.1 ($p<0.05$). Additionally, the H133R mutation significantly increases tethered and lipidated γ2-MSH mediated signaling, an effect not observed with lipidated or tethered BAMS-22. A moderate decrease in signaling with the R55L and F273L variants was observed with both tethered BAMS-22 and tethered γ2-MSH, although this decrease only reached statistical significance with tethered γ2-MSH.

Example 5

The R131S Missense Mutation Reduces the Basal Activity of MrgprX1.

Figure 6:
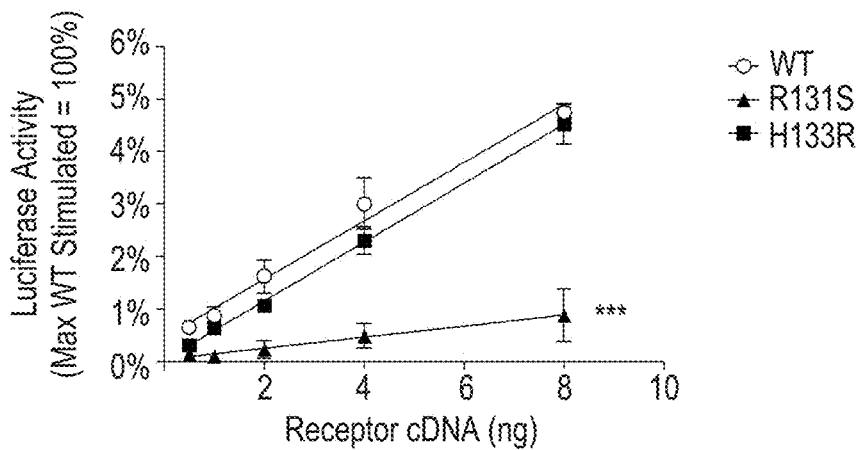
FIG. 6 is a graph showing that the MrgprX1 variant R131S exhibits decreased ligand-independent signaling.

To explore whether changes in receptor-mediated signaling levels in part reflect altered basal activity, ligand-independent signaling of the R131S and the H133R variants was assessed (FIG. 6). HEK293 cells were transfected with cDNAs encoding the corresponding MrpgrX1 variant, an SRE-luciferase reporter construct, and β-galactosidase. After 24 hours, luciferase activity was quantified and normalized relative to β-galactosidase expression. Three independent experiments were performed in triplicate. Data were expressed relative to the maximum signal on wild type MrgprX1 at 3 ng of cDNA, achieved by stimulating with $10^{-5}$ M soluble BAMS-22 for four hours. Results are shown as the mean±SEM and lines were fitted with linear regression. ***, p<0.001 (vs. WT, at 8 ng cDNA). Wild type MrgprX1 exhibits significant basal activity approximating 6% of the maximum BAMS-22 stimulated level of signaling (at 10 µM). The H133R variant shows basal activity levels comparable to WT. In contrast, the R131S variant shows markedly attenuated ligand-independent activity.

Example 6

Expression Levels of the R131S and H133R Variants are Comparable to Wild Type.

The possibility that the observed differences in ligand-dependent and ligand-independent signaling were the result of altered receptor expression was explored. An enzyme-linked immunosorbent assay (ELISA) was used for this analysis. Epitope-tagged versions of WT MrgprX1, and of the R131S and H133R variants were generated. Each receptor was expressed in HEK293 cells. Both the R131S and H133R variants exhibit levels of total and surface expression comparable to WT MrgprX1 (FIGS. 7A-7B). HEK293 cells were transfected with increasing amounts of cDNA encoding the respective N-terminally HA epitope tagged MrgprX1 variant. After 24 hours, surface (FIG. 7A) and total (FIG. 7B) expression levels were assessed by ELISA using non-permeabilized and permeabilized cells, respectively. Differences between expression levels of the WT receptor and the R131S and H133R variants are not statistically significant (p>0.05). After subtraction of background signal (no cDNA transfected), data were expressed relative to maximum wild type MrgprX1 expression in permeabilized cells (total expression). Results are shown as the mean±SEM and lines were fitted with linear regression. These data suggest that observed differences in signaling are not attributable to changes in receptor expression.

Example 7

Production of a Lipidated BAMS-22 Construct (Stable Peptide-Linker-Lipid) Targeting Human MrgprX1

Figure 8:
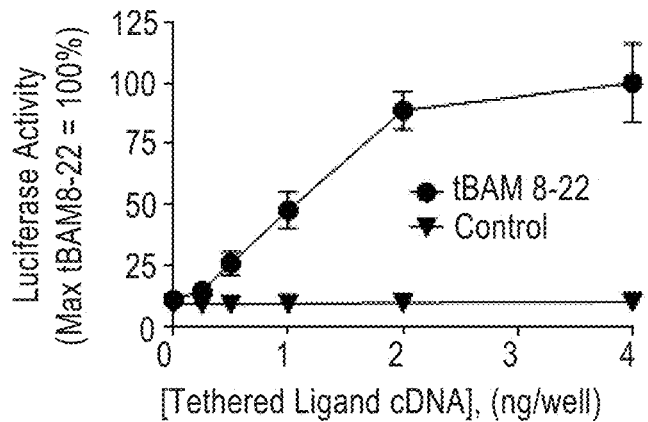
FIG. 8 is a graph showing that recombinant membrane tethered BAMS-22 activates MrgprX1.

In FIG. 8, a luciferase reporter gene assay in HEK293 cells was used to assess tethered ligand induced receptor activity. Cells were transiently co-transfected with cDNAs encoding: MrgprX1, a tethered ligand (as indicated), an SRE-luciferase reporter gene (to assess Gaq signaling), and β-galactosidase control gene (to correct for interwell variability). Luciferase activity was assessed after 24 hours. FIG. 8 demonstrates that recombinant membrane tethered BAMS-22 activates MrgprX1.

Figure 9:
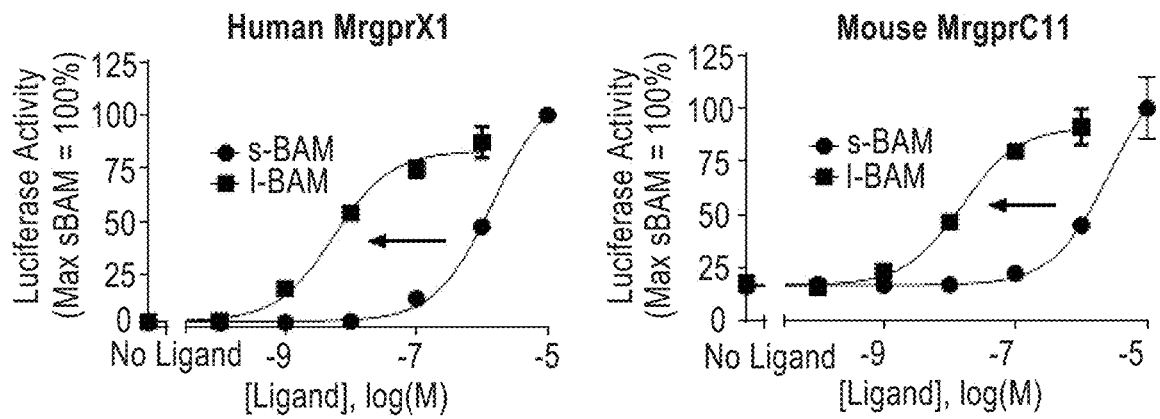
FIG. 9 is a graph showing that the lipidated BAMS-22 analog ('l-BAM') has ~100 fold higher potency than its endogenous BAMS-22 counterpart ('s-BAM').

Based on design of the active BAM MTL (free extracellular N terminus of the peptide, anchored C terminus), a lipidated BAM construct was generated. This lipidated analog (peptide-linker-lipid) comprises an endogenous BAMS-22 peptide, a PEG-8 linker with a KGG spacer, and a palmitic acid membrane anchor. In FIG. 9, a luciferase reporter gene assay in HEK293 cells was used to assess ligand (soluble or lipidated) induced receptor activity. Cells were transiently co-transfected with cDNAs encoding: human MrgprX1 or mouse MrgprC11, an SRE-luciferase reporter gene (to assess Gaq signaling), and β-galactosidase control gene (to correct for interwell variability). Luciferase activity was assessed after 4 hours.

FIG. 9 shows that the lipidated BAMS-22 analog ('l-BAM') has ~100 fold higher potency than its endogenous BAMS-22 counterpart ('s-BAM'). Notably, the lipidated ligands are active on both human and mouse receptor orthologs which supports the validity of using mouse as an in vivo model The generation of a lipidated BAMS-22 construct with enhanced stability follows a stepwise progression.

(i) Identification of Residues that can Tolerate Substitution.

Figure 10:
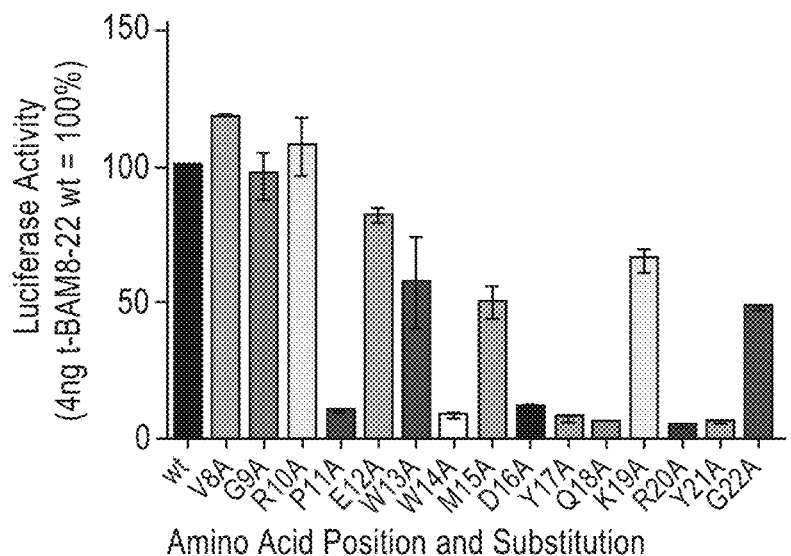
FIG. 10 is a schematic showing amino acid positions in the BAM8-22 peptide considered candidates for modification.

In FIG. 10, a luciferase reporter gene assay in HEK293 cells was used to assess tethered ligand induced receptor activity. To define residues important for ligand-receptor interaction, an alanine scan was performed on the BAMS-22 MTL. This provided an initial index of residues that could be modified without a significant loss of activity. In the seven positions where conversion to alanine resulted in complete loss of function, we also made a series of conservative substitutions based on the categorization of amino acids into the following subgroups: small, nucleophilic, hydrophobic, aromatic, acidic, and basic. With this approach, activity was restored in three of the seven constructs (positions 14, 16, 17; data not shown). In total, 11 positions in the BAMS-22 peptide were thus considered candidates for modification as outlined below (FIG. 10).

(ii) Utilization of Predictive Algorithms to Guide Generation of Protease Resistant Peptides.

Figure 11:
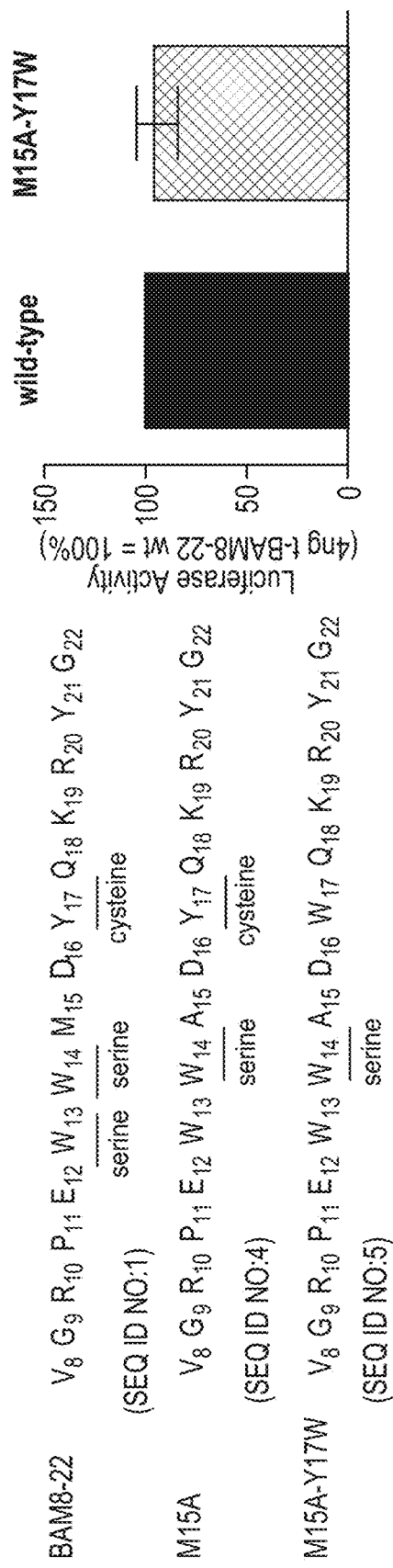
FIG. 11 is a schematic showing amino acid positions in the BAM8-22 predicted to be specifically cleaved by protease family members (underlined).

The BAMS-22 sequence was analyzed using the Protease Specificity Prediction Server (PROSPER) to identify protease sites. PROSPER recognizes aspartic, cysteine, metallo, and serine protease families. In our initial analysis of endogenous BAMS-22, cleavage sites for serine proteases (position 13 and position 14) as well as cysteine proteases (position 17) were observed (FIG. 11). Analysis of active MTLs from the alanine scan, illustrated that the M15A substitution resulted in removal of the cleavage site at position 13. When combined with an additional modification based on the conservative substitution experiments (Y17W), this double substituted analog (M15A-Y17W) showed full activity with no predicated protease activity at either position 13 (serine protease) or position 17 (cysteine protease. To remove the residual serine protease activity at position 14, additional modifications will be introduced in this position (described below). In FIG. 11, underlined residues indicate positions predicted to be specifically cleaved by protease family members. A luciferase reporter gene assay in HEK293 cells was used to assess tethered ligand induced receptor activity.

(iii) Generation of Candidate Protease Resistant MTLs

Amino acid substitutions at position W14 will be incorporated into the M15A-Y17W MTL construct using oligonucleotide-directed, site-specific mutagenesis. Residue substitutions that will eliminate the one remaining serine protease site include; A, R, D, H, V, and P. As an alternative combination of amino acids conferring protease resistance to BAMS-22, substitutions at position W14 will also be introduced into a M15A-D16E MTL. Analysis of this variant is predicted to remove similar protease cleavage sites and is likely to be as active as endogenous BAMS-22 based on conservative substitution experiments (data not shown).

(iv) Assessment of MTL Activity (Gaq Mediated Signaling)

HEK293 cells will be co-transfected with cDNA encoding the MTL variants as outlined above, an SRE luciferase construct and either the human MrgprX1 or the mouse ortholog. Activity will be quantified using a luciferase reporter gene. Several optimized peptide ligands which are predicted to be protease resistant are expected to be identified. The BAM analogs corresponding to the four most active MTLs will then be synthesized as soluble peptides to confirm protease resistance.

(v) Experimental Confirmation of Protease Resistance with Soluble Peptides

Figure 12:
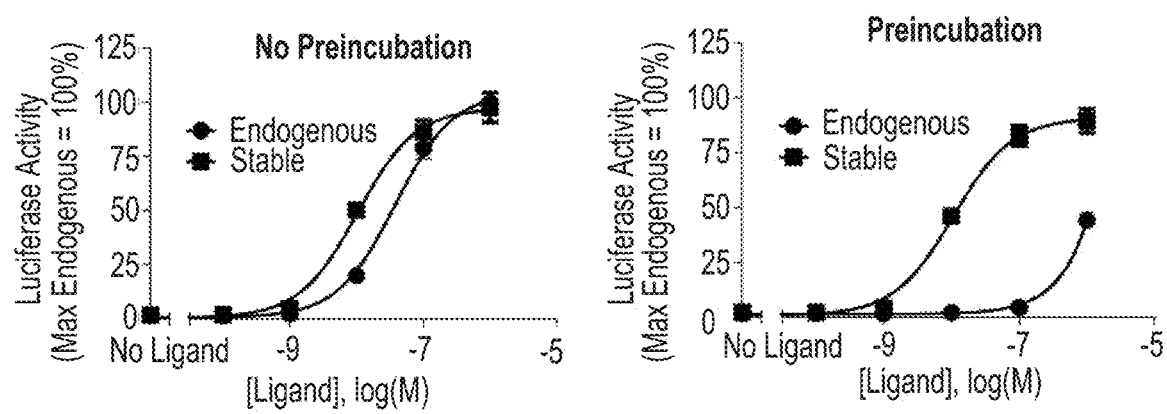
FIG. 12 is a graph showing exposure of ligands to endogenous peptidases in the presence of live cells.

The activity of four newly generated soluble ligands will be assessed after a 24-hour incubation in the presence of live cells (e.g. HEK293 cells or a neuronal cell line). The incubation results in an extended exposure to endogenous peptidases. This methodology is well-established and has been utilized to assess a short, stable chemerin analog. FIG. 12 illustrates the feasibility of this approach and the sustained activity of a stable chemerin analog in comparison to the corresponding short, endogenous sequence. In FIG. 12, a luciferase reporter gene assay in HEK293 cells was used to assess ligand-induced receptor activity. Ligands were either added fresh (no pre-incubation) or pre-incubated with cells overnight (exposure to endogenous peptidases) and then transferred onto transfected cells. Luciferase activity was assessed after a 4 hour stimulation with indicated ligand.

(vi) Chemical Synthesis of Protease Resistant SMALs

Based on the studies outlined above, up to four BAM variant sequences will be incorporated into the following cassette: peptide-PEG8 linker-palmitic acid anchor. In brief, the constructs will be assembled using standard Fmoc chemistry on solid phase resins. An amide or acid C-terminal end can be obtained based on the identity of the resin. A bifunctional (amine and acid derivatized) PEG8 linker will be used that is protected on the amino end. After coupling to the peptide chain, the amine will be unmasked and coupled to the anchor possessing a free acid terminus. The entire construct will be cleaved from the solid phase using TFA/TES/H2O/EDT that results in the simultaneous removal of the side chain protecting groups. Compounds will be purified using reversed-phase HPLC using binary gradients of H2O and acetonitrile containing 0.1% TFA.

(vii) Pharmacological Assessment of SMALs

Up to four SMALs (as outlined above) will be characterized using the series of assays described below. Control ligands will include: SMAL peptide minus lipid (to assess the contribution of lipidation to activity) and a scrambled BAMS-22 peptide (negative control). Gaq signaling: Efficacy and potency of SMALs will be determined using a luciferase reporter gene assay (outlined above) in HEK293 cells expressing either the human MrgprX1 receptor or the mouse ortholog. Wash resistant activity: To determine the extent of anchoring, the luciferase activity assay will be completed with and without serial washing after addition of the ligand. Resistance to washing (an index of lipid anchoring) will be measured in cells incubated with ligand for 15 minutes, washed 3 times using ligand free media, and further incubated for 4 hours.

In acknowledgement that species differences exist within the Mrgprs that can alter receptor mediated function, optimized ligands will be tested on both mouse and human receptors. Constructs that do not show interspecies differences will be preferentially used for in vivo experiments. A protease resistant sequence will likely be found using the recombinant MTL approach (encoding endogenous amino acids). To further complement these efforts, backbone cyclization and incorporation of unnatural amino acids into SMALs at tolerated positions will further enhance stability. Based on the activity of the lipidated BAMS-22 construct, altering the anchor is not anticipated. However, if further optimization is required, the option of introducing other lipids into the SMAL, including: unsaturated fatty acids to increase membrane fluidity (e.g., oleic acid), cholesterol to target different domains of the membrane (e.g., lipid rafts), or alternative hydrocarbon anchors (e.g., stearic acid) to alter hydrophobic mismatch is possible.

Example 8

In Vivo Assessment of Modified BAM8-22.

Figure 13:
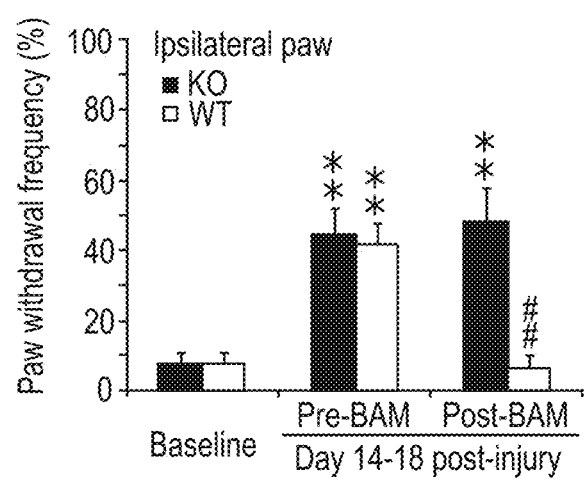
FIG. 13 is a graph showing the inhibitory effect of soluble BAMS-22 on neuropathic pain in vivo.

To assess the therapeutic effectiveness of the compounds of the present disclosure on neuropathic pain, the compounds of the present disclosure will be utilized in a mouse model of chronic constriction injury (CCI)-induced neuropathic pain. Previously, intrathecally applied BAMS-22 (as a soluble agonist) was shown to attenuate mechanical allodynia which was blocked in Mrgpr cluster knockout mice. Using a mouse model of CCI, we show that soluble BAMS-22 inhibits neuropathic pain in vivo. FIG. 13 shows this effect 30 minutes after intrathecal injection of ligand. Using a similar model system (spinal nerve ligation paradigm in rats), the effect of intrathecal BAMS-22 is transient and returns to baseline 90 minutes after administration. In FIG. 13, BAM 8-22 (0.5 mM, 5 µL, intrathecal) attenuates mechanical pain hypersensitivity induced by CCI of the sciatic nerve. Paw withdraw frequency of the ipsilateral hind paw to low-force (0.07 g) was increased 14-18 days post injury. Pain was reduced 30 minutes following intrathecal administration of BAMS-22.

Briefly, after intrathecal administration of drug, a series of von Frey filaments will be applied to the plantar surface of the hind paw and paw withdrawal frequency of the ipsilateral hind paw determined (the contralateral hind paw will be used as a control). There are several considerations. It is anticipated that these lipidated analogs will show enhanced efficacy and longevity versus the prototype lipidated BAMS-22 or its soluble counterpart. Endogenous soluble BAMS-22 already shown to reduce neuropathic pain and will be tested as a positive control. Lipidated BAMS-22 and additional compounds will be assessed for comparison. In order to determine the length of effect of compounds in vivo, multiple time points (30 min, 1 hr, 3 hr, 6 hr, 24 hr, and 3 days) will be assessed following intrathecal injection of ligand.

What is claimed is:

1. A composition comprising a bovine adrenal medulla peptide 8-22 (BAMS-22) peptide coupled to a lipid anchor through a synthetic linker, wherein:
   the BAMS-22 peptide comprises the amino acid sequence of SEQ ID NO: 1; or
   the BAMS-22 peptide comprises an amino acid modification selected from a M to A substitution at position 15 of SEQ ID NO: 1 (M15A), and a Y to W substitution at position 17 of SEQ ID NO: 1 (Y17W); and
   the synthetic linker and the lipid anchor are coupled to the C-terminus of the BAMS-22 peptide.

2. The composition of claim 1, wherein the BAMS-22 peptide comprises M15A and Y17W amino acid modifications.

3. A pharmaceutical composition comprising a composition of claim 1 and a pharmaceutically acceptable carrier.

4. A method of treating neuropathic pain in a subject in need thereof comprising administering to the subject a therapeutically effective amount of a composition of claim 1.

5. The method of claim 4, wherein the subject is a mammal.

6. A method of treating ocular pain in a subject in need thereof comprising administering to the subject a therapeutically effective amount of a composition of claim 1.

7. The method of claim 6, wherein the subject is a mammal.

8. A method of treating ocular inflammation in a subject in need thereof comprising administering to the subject a therapeutically effective amount of a composition of claim 1.

9. The method of claim 8, wherein the subject is a mammal.

10. A method of treating dry eye in a subject in need thereof comprising administering to the subject a therapeutically effective amount of a composition of claim 1.

11. The method of claim 10, wherein the subject is a mammal.

* * * * *